(12) United States Patent
Morita et al.

(10) Patent No.: US 9,737,661 B2
(45) Date of Patent: Aug. 22, 2017

(54) INFUSION SPEED MEASUREMENT INSTRUMENT

(71) Applicant: TATSUTA ELECTRIC WIRE & CABLE CO., LTD., Higashiosaka-shi, Osaka (JP)

(72) Inventors: Takashi Morita, Kizugawa (JP); Hiroshi Araki, Kizugawa (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 81 days.

(21) Appl. No.: 14/762,798

(22) PCT Filed: Jan. 14, 2014

(86) PCT No.: PCT/JP2014/050419
§ 371 (c)(1),
(2) Date: Jul. 22, 2015

(87) PCT Pub. No.: WO2014/115597
PCT Pub. Date: Jul. 31, 2014

(65) Prior Publication Data
US 2015/0352278 A1    Dec. 10, 2015

(30) Foreign Application Priority Data

Jan. 23, 2013 (JP) ................................. 2013-010246

(51) Int. Cl.
*A61M 5/168* (2006.01)
*G01F 1/00* (2006.01)

(52) U.S. Cl.
CPC ............. *A61M 5/1689* (2013.01); *G01F 1/00* (2013.01)

(58) Field of Classification Search
CPC ............................... A61M 5/1689; G01F 1/00
See application file for complete search history.

(56) References Cited

U.S. PATENT DOCUMENTS

| 3,563,090 A | * | 2/1971 | Deltour | A61M 5/1689 |
| | | | | 128/DIG. 13 |
| 3,609,379 A | * | 9/1971 | Hildebrandt | A61M 5/1689 |
| | | | | 128/DIG. 13 |

(Continued)

FOREIGN PATENT DOCUMENTS

| JP | S57501942 A | 11/1982 |
| JP | S60-116340 U | 8/1985 |

(Continued)

OTHER PUBLICATIONS

International Search Report in connection with underlying PCT application PCT/JP2014/050419.

(Continued)

*Primary Examiner* — David Bolduc
(74) *Attorney, Agent, or Firm* — KMF Patent Services, PLLC; Kenneth Fagin; S. Peter Konzel

(57) ABSTRACT

An infusion speed measurement instrument 1 includes: a housing 12 which includes a fitting recessed part 10 in which a side wall 2a of a drip chamber 2 hung in an up-down direction is detachably fitted and a positioning contact part 11 which is in contact with a lower surface 23a of a flange part 23 of the drip chamber 2 fitted in the fitting recessed part 10; an infusion fluid detector 13 which is provided in the housing 12 and is configured to detect infusion fluid 4 dropping from a pipe 32 of the drip chamber 2 which is fitted in the fitting recessed part 10 while being in contact with the positioning contact part 11 at the flange part 23.

13 Claims, 11 Drawing Sheets

(56) References Cited

U.S. PATENT DOCUMENTS

| | | | | | |
|---|---|---|---|---|---|
| 4,029,094 | A | * | 6/1977 | Winicki | A61M 5/1689 128/DIG. 12 |
| 4,265,240 | A | * | 5/1981 | Jenkins | A61M 5/36 128/DIG. 12 |
| 4,346,606 | A | * | 8/1982 | Cannon | A61M 5/1689 128/DIG. 13 |
| 4,397,648 | A | | 8/1983 | Knute | |
| 4,448,207 | A | * | 5/1984 | Parrish | A61B 5/201 428/11 |
| 4,533,347 | A | * | 8/1985 | Deckert | A61M 5/1689 604/250 |
| 4,533,350 | A | * | 8/1985 | Danby | A61M 5/1689 604/253 |
| 4,668,216 | A | * | 5/1987 | Martin | A61M 5/1689 604/246 |
| 4,673,820 | A | | 6/1987 | Kamen | |
| 4,681,569 | A | * | 7/1987 | Coble | A61M 5/1689 604/253 |
| 5,088,990 | A | * | 2/1992 | Hivale | A61M 5/1689 604/251 |
| 5,166,667 | A | * | 11/1992 | Jen | A61M 5/1689 128/DIG. 13 |
| 5,331,309 | A | | 7/1994 | Sakai | |
| 5,621,392 | A | * | 4/1997 | Paolini | A61M 5/1689 128/DIG. 13 |
| 5,938,643 | A | | 8/1999 | Lerner | |
| 5,982,289 | A | * | 11/1999 | Kingsley | A61M 5/1689 340/602 |
| 6,083,206 | A | * | 7/2000 | Molko | A61M 5/1689 604/253 |
| 7,918,834 | B2 | * | 4/2011 | Mernoe | A61M 5/1413 604/253 |
| 2004/0171994 | A1 | * | 9/2004 | Goldberg | A61M 5/1689 604/253 |
| 2010/0309005 | A1 | | 12/2010 | Warner et al. | |
| 2013/0085443 | A1 | * | 4/2013 | Lowery | G05D 7/0635 604/65 |
| 2013/0188040 | A1 | * | 7/2013 | Kamen | G06F 19/3418 348/135 |
| 2014/0267709 | A1 | * | 9/2014 | Hammond | G01N 21/85 348/143 |
| 2014/0283620 | A1 | * | 9/2014 | Kolko | G01F 1/05 73/861.41 |
| 2014/0316370 | A1 | * | 10/2014 | Mernoe | A61M 5/1411 604/500 |

FOREIGN PATENT DOCUMENTS

| | | |
|---|---|---|
| JP | S60116340 U | 8/1985 |
| JP | S62500738 A | 3/1987 |
| JP | H2-149202 U | 12/1990 |
| JP | H02149202 U | 12/1990 |
| JP | H03231680 A | 10/1991 |
| JP | H0650651 U | 7/1994 |
| JP | H09192217 A | 7/1997 |
| JP | 5009426 B | 8/2012 |
| JP | 2012245154 A | 12/2012 |
| WO | WO 2011024182 | 3/2011 |
| WO | PCT/JP2014/050419 | 1/2014 |

OTHER PUBLICATIONS

Extended ESR in re corresponding apn EP 14 74 3231, dated Jun. 27, 2016.

IPRP and Written Opinion from corr'ing PCT app'n PCT/JP2014/050419.

Office Action dated Nov. 8, 2016 in connection with Japanese Patent Application 2013-010246.

Office Action dated May 4, 2017, in corresponding Chinese Patent Application No. 201480005914.5.

Office Action dated May 16, 2017, in corresponding Japanese Patent Application No. 2013-010246.

* cited by examiner

_US 9,737,661 B2_

INFUSION SPEED MEASUREMENT INSTRUMENT

TECHNICAL FIELD

The present invention relates to an infusion speed measurement instrument which is configured to detect infusion speed in a drip chamber.

BACKGROUND

To resolve the inconvenience of calculating infusion speed or the like while visually checking infusion fluid in the drip chamber, a portable infusion speed measurement instrument which is configured to detect infusion fluid by a sensor and notify infusion speed or the like has been proposed. To be more specific, according to propositions (PTL 1 to 3), an infusion speed measurement instrument in which a sensor is provided in a housing capable of pinching the peripheral wall of a drip chamber is provided on the drip chamber in a fixed manner, and infusion speed is notified by detecting infusion fluid dropping in the drip chamber by the sensor through the peripheral wall.

CITATION LIST

Patent Literatures

[PTL 1] Japanese Unexamined Patent Publication No. 03-231680
[PTL 2] Japanese Patent No. 5009426
[PTL 3] Japanese Utility-Model Publication No. 06-50651

SUMMARY OF THE INVENTION

Technical Problem

The known configuration above are disadvantageous in that, depending on the position where the peripheral wall of the drip chamber is pinched and the angle of the pinched peripheral wall of the drip chamber, the detection position of the sensor may be out of the position where the infusion fluid passes, or the dropping infusion fluid may not be detected as the drip chamber is inclined on account of imbalance in the weight of the drip chamber. As such, the detection of the infusion fluid may be inaccurate.

The present invention has been done to solve the problem above, and an object of the present invention is to provide an infusion speed measurement instrument which is easily attached, is capable of accurately detecting infusion speed, and excels in workability when confirming the infusion speed.

Solution to Problem

An infusion speed measurement instrument of the present invention includes: a housing which includes a fitting recessed part in which a side wall of a drip chamber hung in an up-down direction is detachably fitted and a positioning contact part which is in contact with a lower surface of a flange part of the drip chamber fitted in the fitting recessed part; an infusion fluid detector which is provided in the housing and is configured to detect infusion fluid dropping from a pipe of the drip chamber which is fitted in the fitting recessed part while being in contact with the positioning contact part at the lower surface of the flange part; and an information output unit which is configured to output infusion information based on detection of the infusion fluid by the infusion fluid detector.

According to this configuration, the housing is positioned in the horizontal directions with respect to the drip chamber by fitting the side wall of the drip chamber hung in the up-down direction in the fitting recessed part of the infusion speed measurement instrument. Furthermore, the housing is positioned in the up-down directions with respect to the drip chamber by allowing the positioning contact part of the infusion speed measurement instrument to be in contact with the lower surface of the flange part of the drip chamber. As such, by conducting a simple attaching operation to press the fitting recessed part of the housing onto the drip chamber in the horizontal and the up-down directions, the infusion speed measurement instrument is positioned in the horizontal and up-down directions with respect to the predetermined passing point where the infusion fluid dropping from the pipe of the drip chamber passes. Because the infusion fluid is certainly detected by the infusion fluid detector on account of the positioning of the infusion fluid detector provided in the housing with respect to the predetermined passing point of the infusion fluid, the infusion speed is precisely detected so that it can be output in the form of display, sound, or the like by the information output unit. In addition to the above, the positioning of the housing with respect to the drip chamber is achieved only by pressing the housing onto the drip chamber so that this operation can be done by one hand. The workability is therefore excellent because, for example, the user is able to adjust a clamp by the other hand while checking whether the measured infusion speed meets predetermined requirements corresponding to the patient. Thereafter, when the adjustment of the predetermined requirement of the infusion speed is completed, the fitting recessed part of the housing is detached from the drip chamber by simply releasing the pressing of the housing onto the drip chamber. As such, the detaching operation of the infusion speed measurement instrument can be very easily done.

In the infusion speed measurement instrument of the present invention, the housing may include peripheral wall which is formed to be cylindrical in shape, a one-side end face wall which closes a one-side end face of the peripheral wall, an other-side end face wall which closes an other-side end face of the peripheral wall, and an anti-rolling member which is formed by deforming a part of the peripheral wall in a radial direction.

According to this configuration, because the housing is formed to be cylindrical in shape, the user is able to handle the infusion speed measurement instrument in a manner similar to writing instruments such as ball-point pens. Furthermore, the anti-rolling member prevents the infusion speed measurement instrument from rolling when it is put on a place such as a desk. In addition to the above, when the housing is cylindrical in shape, a stress which the housing is in contact with other instrument is small as compared to cases where the housing is angular, and hence instruments which are stored along with the infusion speed measurement instrument in a pocket or a bag are less likely to be broken. This improves the portability and easiness in storage of the infusion speed measurement instrument.

In the infusion speed measurement instrument of the present invention, the housing may include a hanging member to which a string member is attachable.

According to the configuration above, as the string member is attached to the hanging member, the infusion speed measurement instrument may have a function similar to loss prevention function which the strap of the mobile phone performs. This facilitates the handling of the infusion speed measurement instrument when it is stored or carried.

The infusion speed measurement instrument of the present invention may include a switch member provided in the housing, which is waterproof and configured to switch on or off power for driving the infusion fluid detector and the information output unit.

According to the configuration above, because the switch member for turning on or off the infusion speed measurement instrument is waterproof, troubles such as poor contact in the switch member when the infusion speed measurement instrument get wet with the infusion fluid and corrosion due to the intrusion of the infusion fluid into the infusion speed measurement instrument are less likely to occur.

In the infusion speed measurement instrument of the present invention, the positioning contact part may include a height adjustment mechanism which is able to adjust the height of the contacting position of the underside of the flange part where the positioning contact part is in contact.

According to this configuration, even if the position of the dropping port of the drip chamber is different, the positional relationship between the predetermined passing point of the infusion fluid and the infusion speed measurement instrument is optimized for the detection of the infusion fluid, by setting, by means of the height adjustment mechanism, the contacting position where the positioning contact part is in contact with the flange part at a desired position of the drip chamber in the up-down directions with respect to the housing. This makes it possible to accurately detect the infusion speed.

The infusion speed measurement instrument of the present invention may include a fixing elastic member which is provided in the fitting recessed part and is configured to pinch the side wall of the drip chamber with force which is not lower than predetermined holding force.

According to the configuration above, when the infusion speed measurement instrument is attached to the drip chamber, the entirety or part of the weight of the infusion speed measurement instrument is supported by the drip chamber thanks to the holding force exerted by the fixing elastic members. This reduces the burden on the user to maintain the infusion speed measurement instrument to be attached to the drip chamber. In particular, when the fixing elastic members hold the drip chamber with the holding force which is sufficient to support the entire weight of the infusion speed measurement instrument, the user is allowed to take his/her hand off from the infusion speed measurement instrument. The workability is therefore excellent.

An infusion speed measurement instrument of the present invention includes: a housing which includes a peripheral wall which is formed to be cylindrical in shape, a one-side end face wall which closes a one-side end face of the peripheral wall, an other-side end face wall which closes an other-side end face of the peripheral wall, a fitting recessed part formed on the one-side end face wall of the peripheral wall and a side wall of a drip chamber hung in an up-down direction is detachably fitted to, a positioning contact part which is in contact with a lower surface of a flange part of the drip chamber fitted in the fitting recessed part, an anti-rolling member which is formed by deforming a part of the peripheral wall in a radial direction, and a hanging member which is formed on the one-side end face wall, to which a string member is attachable; an infusion fluid detector which is configured to detect, in a detection area arranged in the fitting recessed part, infusion fluid dropping from a pipe of the drip chamber fitted in the fitting recessed part while being in contact with the positioning contact part at the lower surface of flange part; an information output unit provided on the other-side end face wall side of the peripheral wall and is configured to output infusion information based on detection of the infusion fluid by the infusion fluid detector; and a switch member provided on the other-side end face wall of the housing, which is waterproof and configured to turn on or off power for driving the infusion fluid detector and the information output unit.

According to this configuration, the housing is positioned in the horizontal direction with respect to the drip chamber by fitting the side wall of the drip chamber hung in the up-down direction in the fitting recessed part of the infusion speed measurement instrument. Furthermore, the housing is positioned in the up-down direction with respect to the drip chamber by allowing the positioning contact part of the infusion speed measurement instrument to be in contact with the lower surface of the flange part of the drip chamber. As such, by conducting a simple attaching operation to press the fitting recessed part of the housing onto the drip chamber in the horizontal and the up-down directions, the infusion speed measurement instrument is positioned in the horizontal and up-down directions with respect to the predetermined passing point where the infusion fluid dropping from the pipe of the drip chamber passes. Because the infusion fluid is certainly detected by the infusion fluid detector on account of the positioning of the infusion fluid detector provided in the housing with respect to the predetermined passing point of the infusion fluid, the infusion speed is precisely detected and output in the form of image display, sound, or the like by the information output unit. In addition to the above, the positioning of the housing with respect to the drip chamber is achieved only by pressing the housing onto the drip chamber, and this operation can be done by one hand. The workability is therefore excellent. Thereafter, when the detection of the infusion speed is completed, the fitting recessed part of the housing is detached from the drip chamber by simply releasing the pressing of the housing onto the drip chamber. As such, the detachment of the infusion speed measurement instrument can be very easily done.

In addition to the above, because the housing is formed to be cylindrical in shape, the user is able to handle the infusion speed measurement instrument in a manner similar to writing instruments such as ball-point pens. Furthermore, the anti-rolling member prevents the infusion speed measurement instrument from rolling when it is put on a place such as a desk. Furthermore, when the housing is cylindrical in shape, a stress which the housing is in contact with other instrument is small as compared to cases where the housing is angular, and hence instruments which are stored along with the infusion speed measurement instrument in a pocket or a bag are less likely to be broken. This improves the portability and easiness in storage of the infusion speed measurement instrument.

In addition to the above, as the string member is attached to the hanging member, the infusion speed measurement instrument may have a function similar to loss prevention function which the strap of the mobile phone performs. Furthermore, because the hanging member to which the string member can be attached is formed on the one-side end face of the housing, the axial direction of the housing can be changed to match the up-down direction when the user holds the string member attached to the hanging member. This facilitates the handling of the infusion speed measurement instrument when it is stored or carried.

Furthermore, because the switch member is provided on the other-side end face of the housing, the switch member can be easily detected by touch, without relying on sight. With this, the infusion speed measurement instrument can be easily turned on or off even if the room is dark. Furthermore, because the switch member is waterproof, troubles such as poor contact in the switch member when the infusion speed measurement instrument is wet with the infusion fluid and corrosion due to the intrusion of the infusion fluid into the infusion speed measurement instrument are less likely to occur.

Advantageous Effect of Invention

The infusion speed measurement instrument can be easily attached, can accurately detect the infusion speed, and excels in the workability while confirming the infusion information.

PREFERRED EMBODIMENT OF THE INVENTION

The following will describe a preferred embodiment of the present invention with reference to figures.

Overall Configuration

Figure 1:
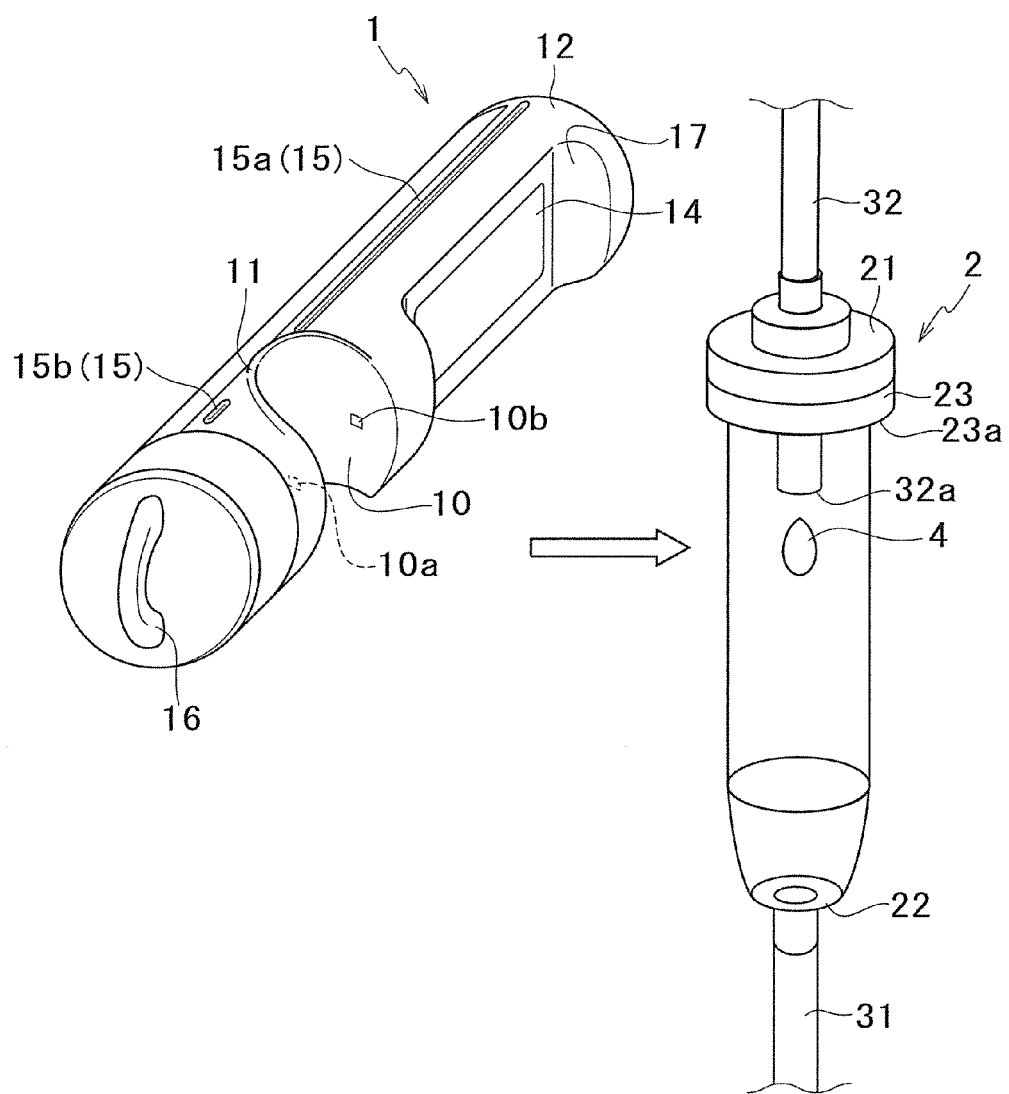
FIG. 1 illustrates a process of attaching an infusion speed measurement instrument to a drip chamber.
Figure 2:
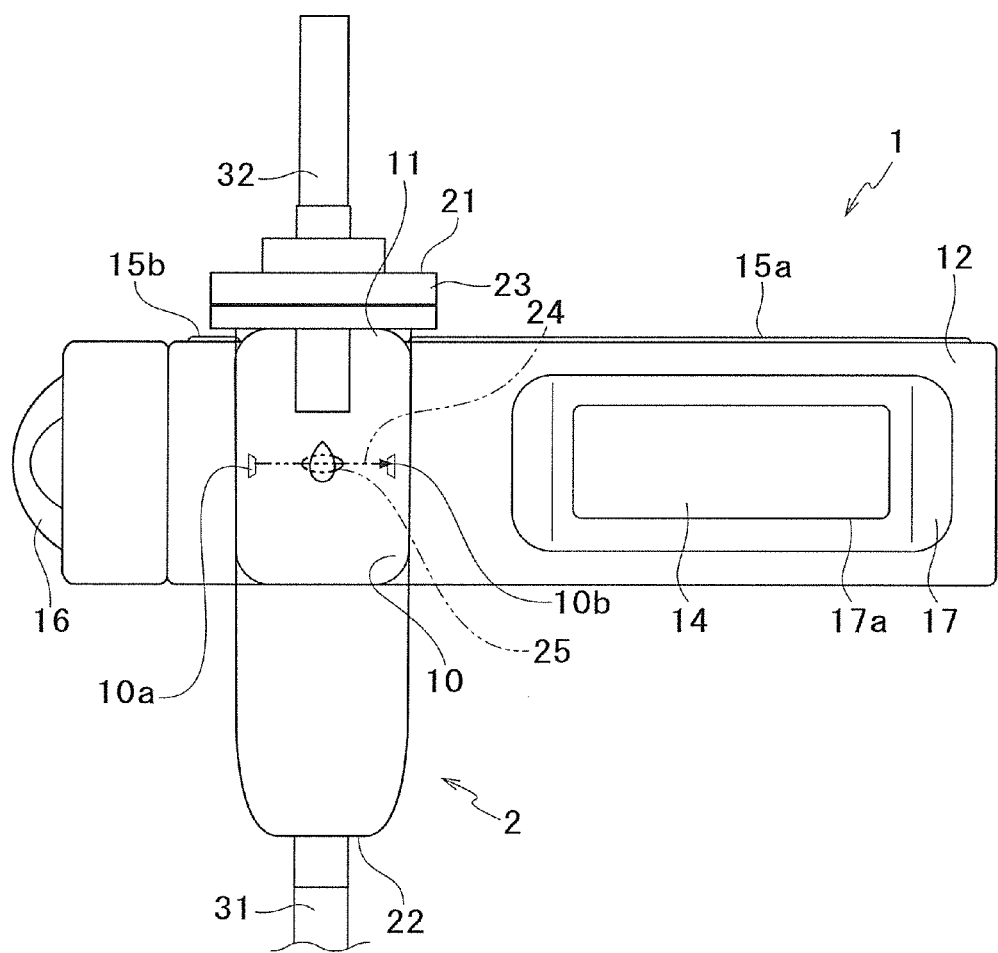
FIG. 2 illustrates a state in which the infusion speed measurement instrument has been attached to the drip chamber.
Figure 3:
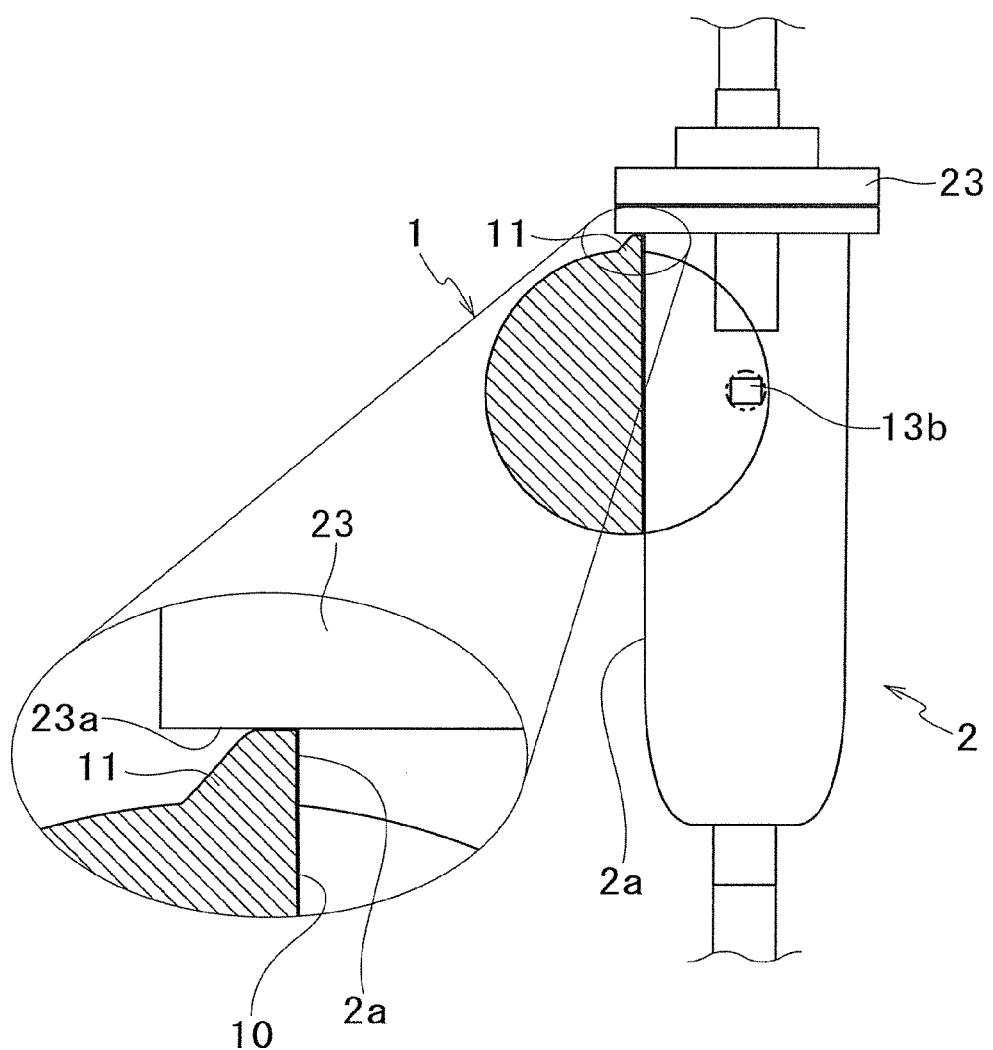
FIG. 3 illustrates a state in which the infusion speed measurement instrument has been attached to the drip chamber.

As shown in FIG. 1 to FIG. 3, an infusion speed measurement instrument 1 of the present embodiment is easily positioned by one hand, with reference to a side wall 2a of a drip chamber 2 which is hung in an up-down direction and a lower surface 23a of a flange part 23 of the drip chamber 2, to set a predetermined passing point 25 of infusion fluid 4 as a detection position. The infusion speed measurement instrument 1 is configured to detect an infusion speed of the infusion fluid 4 at this detection position, and output infusion information based on the detected infusion speed of the infusion fluid 4.

In regard to the above, the detection position is preferably set at a position in the vicinity of a dropping port 32a of a pipe 32. This allows the drip chamber 2 to be variously postured in a wide range in which the infusion fluid 4 is detectable. That is to say, when the detection position is set in the vicinity of the dropping port 32a, the distance between the line connecting the dropping port 32a with the pipe 31 and the line of the dropping of the infusion fluid from the dropping port 32a is short, even if the drip chamber 2 is inclined. On this account, even if the drip chamber 2 is significantly inclined, the infusion fluid is detectable as compared to cases where the infusion fluid 4 is detected at a position remote from the dropping port 32a. The infusion information indicates different types of information regarding infusion. The infusion information in the present embodiment indicates the number of times the infusion fluid 4 drops per unit time, but the infusion information is not limited to this definition. Examples of the infusion information include an infusion speed which indicates how many times the infusion fluid 4 drops per unit time, an infusion number which indicates the total number of times the infusion fluid 4 drops, an infusion total amount which is calculated by multiplying the infusion number by a unit amount of the infusion fluid 4, an infusion amount per a unit time, and an elapsed time of infusion from the start of the infusion. The output of the infusion information encompasses notification of the infusion information to a user of or a patient using the infusion speed measurement instrument 1 by image display on LCD, sound, light, or the like, and transmission of the infusion information to an external device such as an information processor by data communication.

To be more specific, the infusion speed measurement instrument 1 includes: a housing 12 including a fitting recessed part 10 in which the side wall 2a of the drip chamber 2 hung in the up-down direction is detachably fitted and a positioning contact part 11 which is in contact with the lower surface 23a of the flange part 23 of the drip chamber 2 fitted in the fitting recessed part 10; an infusion fluid detector 13 which is provided in the housing 12 and is configured to detect the infusion fluid 4 dropping from a pipe of the drip chamber 2 which is fitted in the fitting recessed part 10 so that the lower surface of the flange part 23 is in contact with the positioning contact part 11; and an information output unit 14 which is configured to output infusion information based on the detection of the infusion fluid 4 by the infusion fluid detector 13.

With this configuration, the housing 12 is positioned in the horizontal direction with respect to the drip chamber 2 by fitting the side wall 2a of the drip chamber 2 hung in the up-down direction in the fitting recessed part 10 of the infusion speed measurement instrument 1. Furthermore, the housing 12 is positioned in the up-down direction with respect to the drip chamber 2 by allowing the positioning contact part 11 of the infusion speed measurement instrument 1 to be in contact with the lower surface 23a of the flange part 23 of the drip chamber 2. As such, by conducting a simple attaching operation to press the fitting recessed part 10 of the housing 12 onto the drip chamber 2 in the horizontal and the up-down directions, the infusion speed measurement instrument 1 is positioned in the horizontal and up-down directions with respect to the predetermined passing point 25 where the infusion fluid 4 dropping from the pipe 32 of the drip chamber 2 passes. Because the infusion fluid 4 is certainly detected by the infusion fluid detector 13 on account of the positioning of the infusion fluid detector 13 provided in the housing 12 with respect to the predetermined passing point 25 of the infusion fluid 4, the infusion speed is precisely detected and output in the form of image display, sound, or the like by the information output unit 14. In addition to the above, the positioning of the housing 12 with respect to the drip chamber 2 is achieved only by pressing the housing 12 onto the drip chamber 2, and this operation can be done by one hand. The workability is therefore excellent so that the user is able to adjust the infusion speed by operating a clamp 73 by the other hand. Thereafter, when the detection of the infusion information is completed, the fitting recessed part 10 of the housing 12 is detached from the drip chamber 2 by simply releasing the pressing of the housing 12 onto the drip chamber 2. As such, the detachment of the infusion speed measurement instrument 1 can be very easily done.

Hereinafter, the side of the infusion speed measurement instrument 1 where the drip chamber 2 is fitted in the fitting recessed part 10 in the horizontal direction will be referred to as the front surface side.

Housing 12

Figure 4:
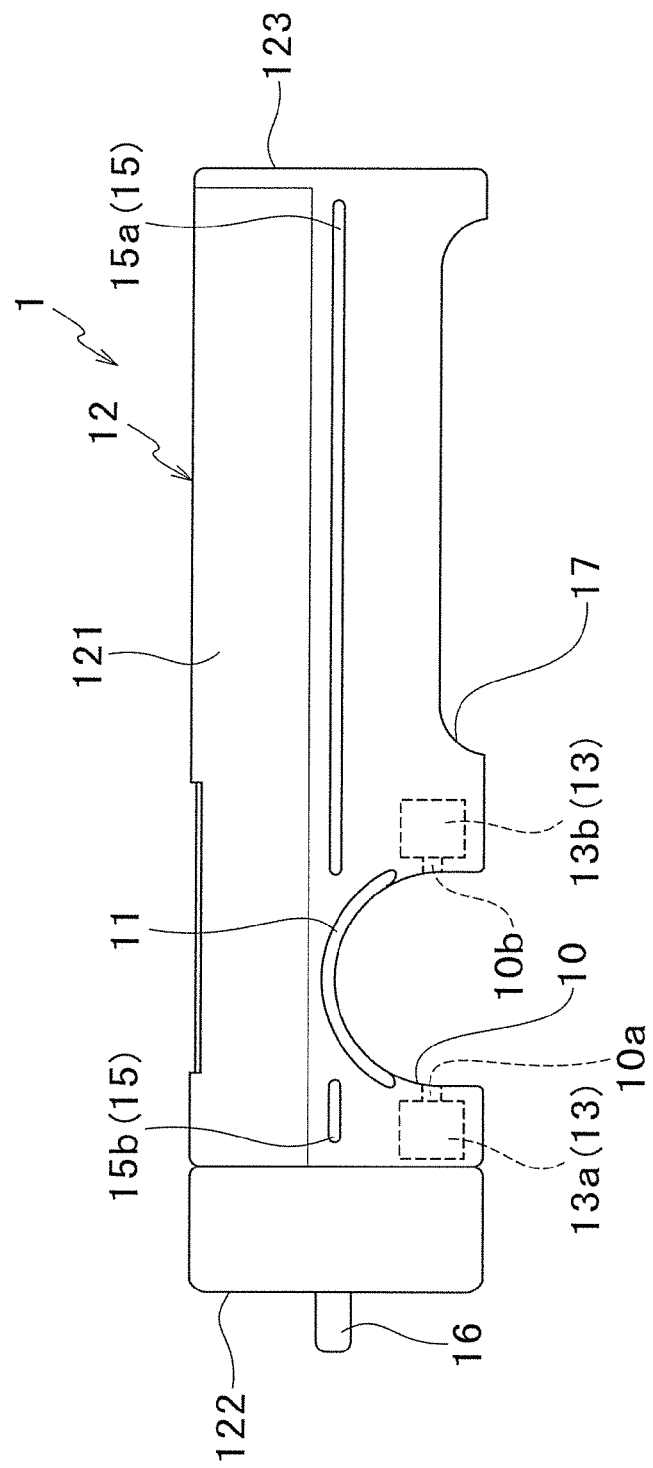
FIG. 4 is a top view of the infusion speed measurement instrument.

Now, the infusion speed measurement instrument 1 will be detailed. The housing 12 of the infusion speed measurement instrument 1 has a cylindrical external shape. To be more specific, as shown in FIG. 4, the housing 12 includes a peripheral wall 121 which is formed to be cylindrical in shape, a one-side end face wall 122 which closes the one-side end face of the peripheral wall 121, and an other-side end face wall 123 which closes the other-side end face of the peripheral wall 121.

The housing 12 is not limited to be cylindrical in shape, and may be differently shaped such as rectangular parallelepiped and polygonal pillar.

In the housing 12, the fitting recessed part 10, the positioning contact part 11, an anti-rolling member 15, a hanging member 16, and a mounting part 17 are formed.

In the housing 12, furthermore, the infusion fluid detector 13, the information output unit 14, and the like are provided.

Housing 12: Fitting Recessed Part 10

The fitting recessed part 10 is formed on the front surface side of the peripheral wall 121 of the housing 12 and is close to the one-side end face wall 122. The fitting recessed part 10 is formed in such a way that a part of the peripheral wall 121 is recessed. The fitting recessed part 10 is recessed in accordance with the shape of the drip chamber 2 to be fitted therein. That is to say, as shown in FIG. 4, when viewed from above, the fitting recessed part 10 is formed to have a tunnel shape (U-shaped) and reaches the central axis in the longitudinal direction of the housing 12.

With this, because the side wall 2a of the drip chamber 2 is in contact with the substantially entirety of the fitting recessed part 10 when the drip chamber 2 is pressed onto the fitting recessed part 10, the fitting recessed part 10 is stably attached to the drip chamber 2. Furthermore, in consideration of the tunnel shape, a light emitting hole 10a and a light receiving hole 10b are in the neighborhood of the joints of an arc part and linear parts of the tunnel shape, respectively, to form a line along which infrared light 24 for detecting the infusion fluid 4 dropping from the dropping port 32a at the central part of the drip chamber 2 passes. Furthermore, as the drip chamber 2 is fitted in the fitting recessed part 10, the infusion speed measurement instrument 1 is positioned in the horizontal direction with respect to the predetermined passing point 25 where the infusion fluid 4 dropping from the pipe 32 of the drip chamber 2 passes (see FIG. 2).

Furthermore, on account of the tunnel shape, the state of being in contact with the side wall 2a of the drip chamber 2 is easily established and easily canceled.

It is preferable for the fitting recessed part 10 to match the external shape of a typical drip chamber 2 and get narrowed in diameter downward. This allows the infusion speed measurement instrument 1 to be stably attached to the drip chamber 2, and the positioning is precisely carried out.

In addition to the above, in the fitting recessed part 10, the light emitting hole 10a and the light receiving hole 10b penetrating up to the inside are formed at the wall surface on the one-side end face wall 122 side and the wall surface on the other-side end face wall 123 side that face to each other. Through the light emitting hole 10a, light from a later-described infusion fluid detector 13 (light emitter 13a) provided in the housing 12 is emitted. The emitted light is received by an infusion fluid detector 13 (light receiver 13b) through the light receiving hole 10b.

Housing 12: Positioning Contact Part 11

The positioning contact part 11 is formed to be in contact with the lower surface 23a of the flange part 23 of the drip chamber 2 fitted in the fitting recessed part 10. In other words, the positioning contact part 11 is formed by arranging the arc part which is on the upper surface of the peripheral wall 121 and extends along the fitting recessed part 10 to protrude vertically upward.

The flange part 23 is a lid provided at the upper surface part of the drip chamber 2. As the pipe 32 in contact with a through hole (not illustrated) formed in the flange part 23 is inserted into the drip chamber 2, the entirety of the drip chamber 2 is supported by the pipe 32. Through this pipe 32, the infusion fluid 4 is supplied into the drip chamber 2. Because in a typical drip chamber 2 the diameter of the flange part 23 is longer than the diameter of the side wall 2a, the positioning contact part 11 protruding from the upper surface of the infusion speed measurement instrument 1 is allowed to be in contact with the lower surface 23a of the flange part 23.

In this manner, as the lower surface 23a of the flange part 23 of the drip chamber 2 contacts with the positioning contact part 11, the infusion speed measurement instrument 1 is positioned in the up-down direction with respect to the predetermined passing point 25 where the infusion fluid 4 dropping from the pipe 32 of the drip chamber 2 passes.

The predetermined passing point 25 is arranged below the dropping port 32a of the pipe 32 inserted into the drip chamber 2, from which the infusion fluid 4 drops. Furthermore, the predetermined passing point is preferably arranged in the vicinity of the dropping port 32a (i.e., arranged to be close to the dropping port 32a as much as possible). This causes the path of the dropping infusion fluid 4 to be in the detection position, even if the drip chamber 2 to which the infusion speed measurement instrument 1 is attached is inclined.

In addition to the above, the positioning contact part 11 may not have a protruding arc shape. For example, the positioning contact part 11 may be formed of one or more protruding parts, the upper surface of the peripheral wall 121 may protrude more than the above-described arrangement, or the entire upper surface of the peripheral wall 121 may protrude. In accordance with the predetermined passing point 25, the positioning contact part 11 may not protrude or may be recessed to be at least included within the scope of the flange part 23 of the drip chamber 2 therein.

Housing 12: Anti-Rolling Member 15

The anti-rolling member 15 is formed by deforming a part of the peripheral wall 121 of the housing 12 in a radial direction. In the present embodiment, on the upper surface of the peripheral wall 121 of the housing 12, the anti-rolling member 15 is formed to extend along the axial direction of the housing 12. The anti-rolling member 15 includes an anti-rolling member 15a and an anti-rolling member 15b formed respectively at the right and left sides of the positioning contact part 11 sandwiched between anti-rolling member 15a and 15b. The anti-rolling members 15a and 15b protrude in a convex manner toward the outside in the radial direction. With this configuration, when, for example, the cylindrical infusion speed measurement instrument 1 placed on a desk or the like rolls, the anti-rolling member 15 is stuck on the upper surface of the desk so that the rolling motion is stopped.

As long as the anti-rolling member 15 is deformed in the radial direction, the anti-rolling member 15 may be a part of the peripheral wall 121 protruding in a convex manner in the radial direction, may be a recessed part of the peripheral wall 121, or may be a notch formed at a part of the peripheral wall 121.

Housing 12: Hanging Member 16

The hanging member 16 is formed on the one-side end face wall 122 to allow a string member to be attached thereto. To be more specific, the hanging member 16 is formed to be arc-shaped as shown in FIG. 2, and the string member can be attached to the hole between the hanging member 16 and the one-side end face wall 122.

Furthermore, because the hanging member 16 to which the string member can be attached is formed on the one-side end face of the housing 12, the axial direction of the housing 12 can be changed to match to the up-down direction when the user holds the string member attached to the hanging member 16. This further facilitates the handling of the infusion speed measurement instrument when it is stored or carried.

The hanging member 16 may not be formed on the one-side end face wall 122. The hanging member 16 may be formed at any part of the housing 12. For example, two or more holes which are connected with each other inside the housing 12 may be formed in the one-side end face wall 122. Alternatively, a hole penetrating the peripheral wall 121 or a hole which penetrates from the one-side end face wall 122 to the peripheral wall 121 may be formed.

Housing 12: Mounting Part 17

The mounting part 17 is formed to extend from the central part on the front surface side of the peripheral wall 121 toward the other-side end face wall 123 side. A part of the peripheral wall 121 is recessed to form the mounting part 17. The mounting part 17 has a flat mounting surface 17a. The mounting surface 17a is formed to be orthogonal to the normal vector of the housing 12 passing the central part of the mounting part 17 in the radial direction, and this orthogonal direction is substantially in parallel to the direction in which the infusion fluid drops. The mounting surface 17a is formed of a transparent member which is permeable.

This makes it possible to visually check the infusion information displayed by the information output unit 14 which is provided in the housing 12.

Housing 12: Switch Member 20

Figure 5:
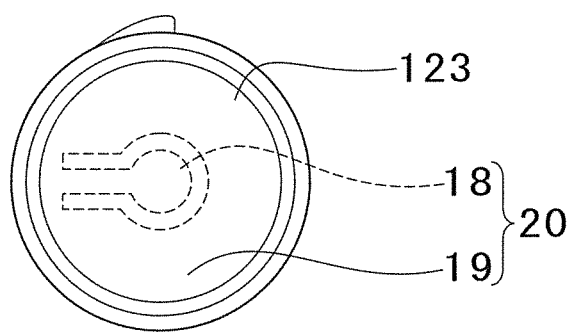
FIG. 5 is a side view of the infusion speed measurement instrument.

As shown in FIG. 5, on the other-side end face wall 123 of the housing 12, a switch member 20 is provided. To be more specific, in the other-side end face wall 123, a push-in part 18 is formed by cutting out the wall 123 except a part of the wall 123. The push-in part 18 can therefore be pushed toward the inside of the housing 12 with the part above functioning as an axis. With this, a later-described input unit 53 provided inside is driven by the push-in part 18, so that the power for driving the infusion fluid detector 13 and the information output unit 14 may be turned on or off. Furthermore, to the other-side end face wall 123 is pasted a waterproof seal 19, so that the front surface of the wall 123 is covered with the waterproof seal 19. This ensures the waterproof performance of the switch member 20.

Furthermore, because the switch member 20 is provided on the other-side end face wall 123 of the housing 12, the switch member 20 can be easily detected by touch, without relying on sight. With this, the power can be easily turned on or off even if the room is dark.

In the present embodiment the push-in part 18 is formed on the other-side end face wall 123 of the housing 12 and the switch member 20 is formed by pasting the waterproof seal 19 to cover the other-side end face wall 123. However, the embodiment is not limited to this.

Disassembled Structure of Housing 12

Figure 6:
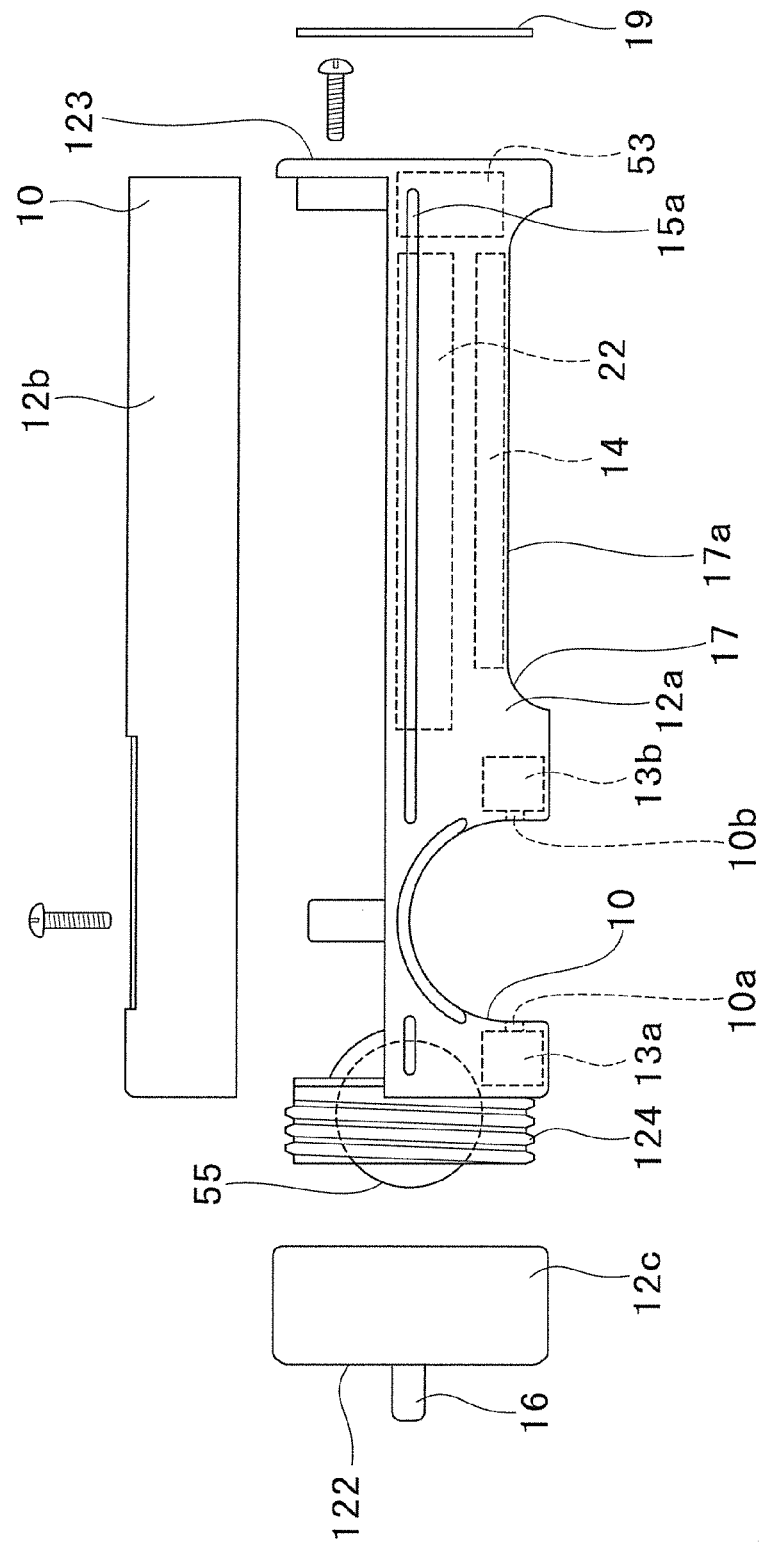
FIG. 6 is an exploded view of the infusion speed measurement instrument.

As shown in FIG. 6, the housing 12 is constituted by a front surface part 12a which constitutes the front surface side of the housing 12, a rear surface part 12b which constitutes the rear surface side of the housing 12, and a cap part 12c which constitutes the one-side end face wall 122 side.

The front surface part 12a houses members such as the infusion fluid detector 13 (the light emitter 13a and the light receiver 13b), the information output unit 14, the input unit 53, a later-described control board 22, and cables (not illustrated) connecting these members. On the one-side end face wall 122 of the front surface part 12a, a screw part 124 having a screw structure on its peripheral surface is formed. The screw part 124 is hollow inside and is able to house an electricity storage part of a later-described power source 55.

The rear surface part 12b is fitted to cover the members such as the infusion fluid detector 13 (the light emitter 13a and the light receiver 13b), the information output unit 14, the input unit 53, the later-described control board 22, and the cables (not illustrated) connecting these members, which are housed in the front surface part 12a. Furthermore, the rear surface part 12b is fixed to the front surface part 12a by screws, on the other-side end face wall 123 side and on the rear surface side.

Inside the cap part 12c is provided with a female screw hole (not illustrated) screwed with the screw part 124 formed on the front surface part 12a. With this, the cap part 12c is fitted to the screw part 124 to cover the power source 55.

Information Output Unit 14

Inside the housing 12 of the mounting part 17, the information output unit 14 is provided. The information output unit 14 is configured to output infusion information based upon the detection of the infusion fluid 4 by the infusion fluid detector 13. In the present embodiment the information output unit 14 is a liquid crystal display device and notifies the infusion information by means of image display, but it is not limited to this. For example, the infusion information may be notified by sound, or vibration. Alternatively, the infusion information may be notified by a combination of them. The information output unit 14 is provided to be in contact with the inside of the housing 12 of the mounting surface 17*a*.

Control Board 22

Figure 7:
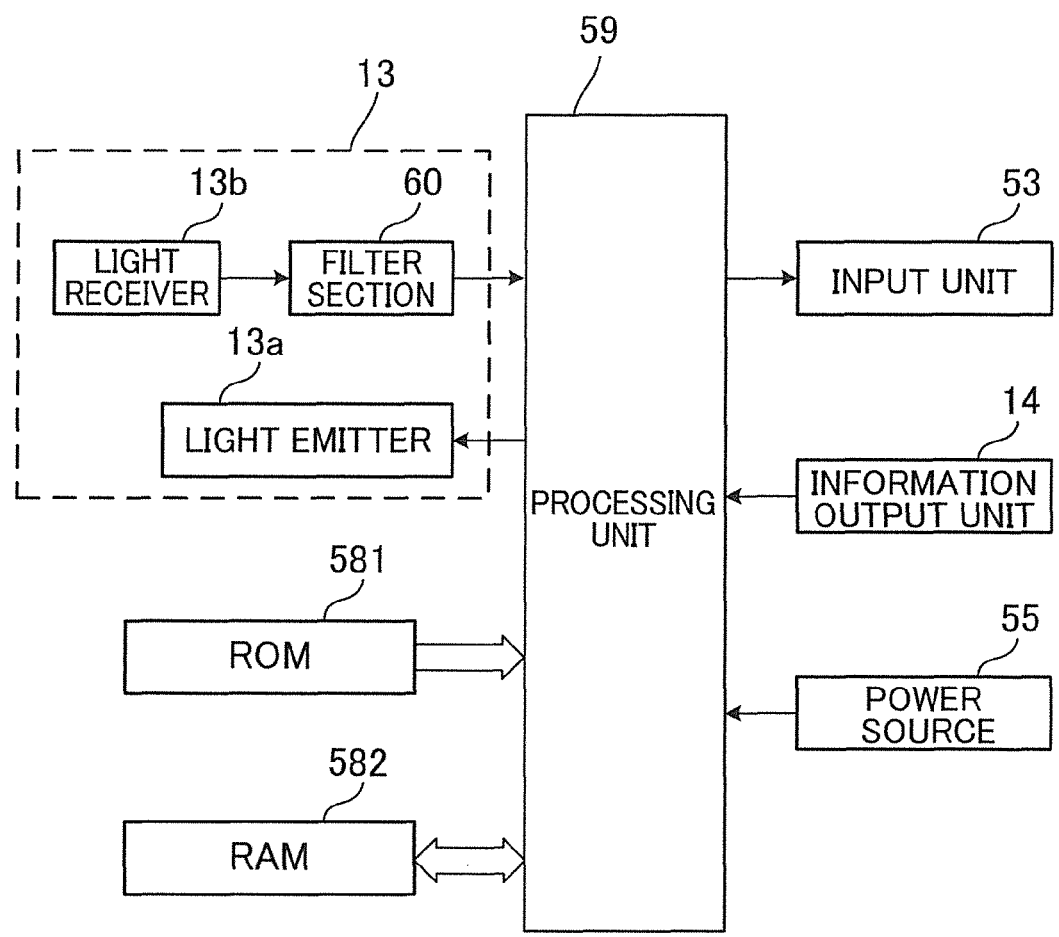
FIG. 7 is a control block diagram of an information output unit.

Inside the housing 12 is provided the control board 22. As shown in FIG. 7, the control board 22 includes a processing unit 59 capable of executing programs, a ROM 581 and a RAM 582 which are storage means connected to the processing unit 59, and a filter section 60. The ROM 581 stores programs such as a control program and data for controlling the infusion speed measurement instrument 1. The RAM 582 stores changeable setting information. In the present embodiment a non-volatile memory is adopted as the RAM 582 in order to store the setting information after the power off, but it is not limited to this. Furthermore, the processing unit 59 is connected to the input unit 53, the information output unit 14, and the power source 55.

The power source 55 includes an electricity storage part which is a battery, a large-capacity capacitor, or the like and a power supplying part which is configured to supply power at a voltage suitable for the information output unit 14 and the infusion fluid detector 13.

The information output unit 14 may be configured such that a touch panel is provided on the front surface of the information output unit 14 and different types of infusion information are switched based upon the input of a detailed instruction or data through the touch panel.

Infusion Fluid Detector 13

In addition to the above, the processing unit 59 is connected with the infusion fluid detector 13 via the filter section 60. The infusion fluid detector 13 includes the light emitter 13*a* which is configured to emit light with a predetermined light intensity and the light receiver 13*b* which is configured to output a detection signal when the received light intensity is equal to or lower than a threshold value.

The light emitter 13*a* is formed of a light emitting diode. The light emitting diode is provided inside the light emitting hole 10*a* which is formed in the fitting recessed part 10. In the meanwhile, the light receiver 13*b* includes a photo diode which is not illustrated. The photo diode is provided inside the light receiving hole 10*b* which is formed in the fitting recessed part 10. The light from the light emitter 13*a* is therefore emitted to the outside of the housing 12 through the light emitting hole 10*a*. The light emitted to the outside of the housing 12 is configured to traverse the space formed by the fitting recessed part 10, and reaches the light receiver 13*b* through the light receiving hole 10*b*. With this configuration, when the drip chamber 2 is fitted in the fitting recessed part 10, the infusion fluid 4 dropping in the drip chamber 2 blocks the light emitted from the light emitter 13*a*. The light receiver 13*b* transmits the light intensity level of the received light to the processing unit 59 via the filter section 60. The light intensity level is properly corrected by the filter section 60, and the processing unit 59 detects intervals of blocking of the light.

In other words, the infusion fluid detector 13 is able to detect the blocking of emitted light by the infusion fluid 4.

Now, the filter section 60 will be specifically described. The filter section 60 includes an unillustrated circuit having an AC coupling function, and minimizes the influence of disturbance light on the light received by the light receiver 13*b*.

To be more specific, the light received by the light receiver 13*b* is an aggregate of the infrared light from the light emitter 13*a* and the disturbance light corresponding to the installation environment of the infusion speed measurement instrument 1.

In the present embodiment, the light intensity level received by the light receiver 13*b* is filtered by the AC coupling function of the filter section 60 and is then transmitted to the processing unit 59. With this, a DC component signal generated by the disturbance light from a room light or the like is eliminated. The light intensity level received by the processing unit 59 is therefore less influenced by the disturbance light.

Operation of Attaching Infusion Speed Measurement Instrument 1

Figure 8:
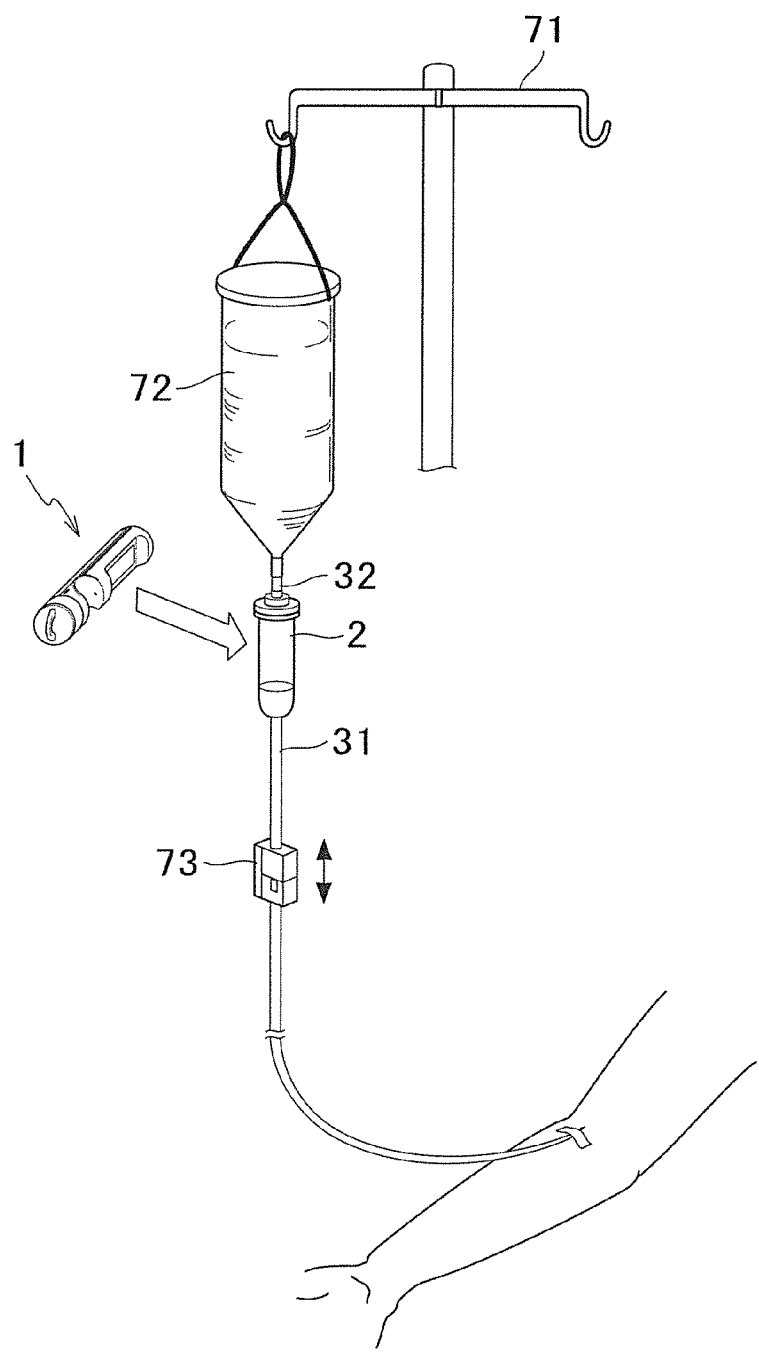
FIG. 8 shows the infusion speed measurement instrument which is in use.

To begin with, as shown in FIG. 8, the drip chamber 2 is attached via the pipe 32 to a chemical container 72 hung from a stand 71, and the clamp 73 is attached to the drip chamber 2 via the pipe 31. As an injection needle is inserted into an arm or the like of a patient, the preparation of the injection is completed.

Subsequently, the infusion speed measurement instrument 1 is attached to the drip chamber 2. To be more specific, as shown in FIG. 1, the infusion speed measurement instrument 1 is moved from one side of the drip chamber 2, and the drip chamber 2 is housed in the fitting recessed part 10 of the infusion speed measurement instrument 1. With this, the infusion speed measurement instrument 1 is positioned in the horizontal direction. Then the infusion speed measurement instrument 1 is moved upward or the drip chamber 2 is moved downward, until the lower surface 23*a* of the flange part 23 of the drip chamber 2 becomes in contact with the positioning contact part 11 of the infusion speed measurement instrument 1. As a result, the infusion speed measurement instrument 1 is positioned in the up-down direction and the attachment of the infusion speed measurement instrument 1 is completed.

It is noted that the power on by means of the switch member 20 may be carried out before or after the attachment of the infusion speed measurement instrument 1.

Operations of Infusion Speed Measurement Instrument 1

Now, operations of the infusion speed measurement instrument 1 will be described.

Power Source Program

The following will describe a power source program for the infusion speed measurement instrument 1 after the switch member 20 is operated and the input unit 53 is operated (powered on or off). It is noted that the infusion speed measurement instrument 1 of the present embodiment is configured such that a unit time for the number of times of dropping can be set at the power on. To be more specific, the unit time within which the number of times of dropping is measured can be set to either 60 seconds or 10 seconds.

The unit time is not limited to these values. Furthermore, the unit time for the number of times of dropping may not be changeable, or may be selected from three or more types.

Figure 9:
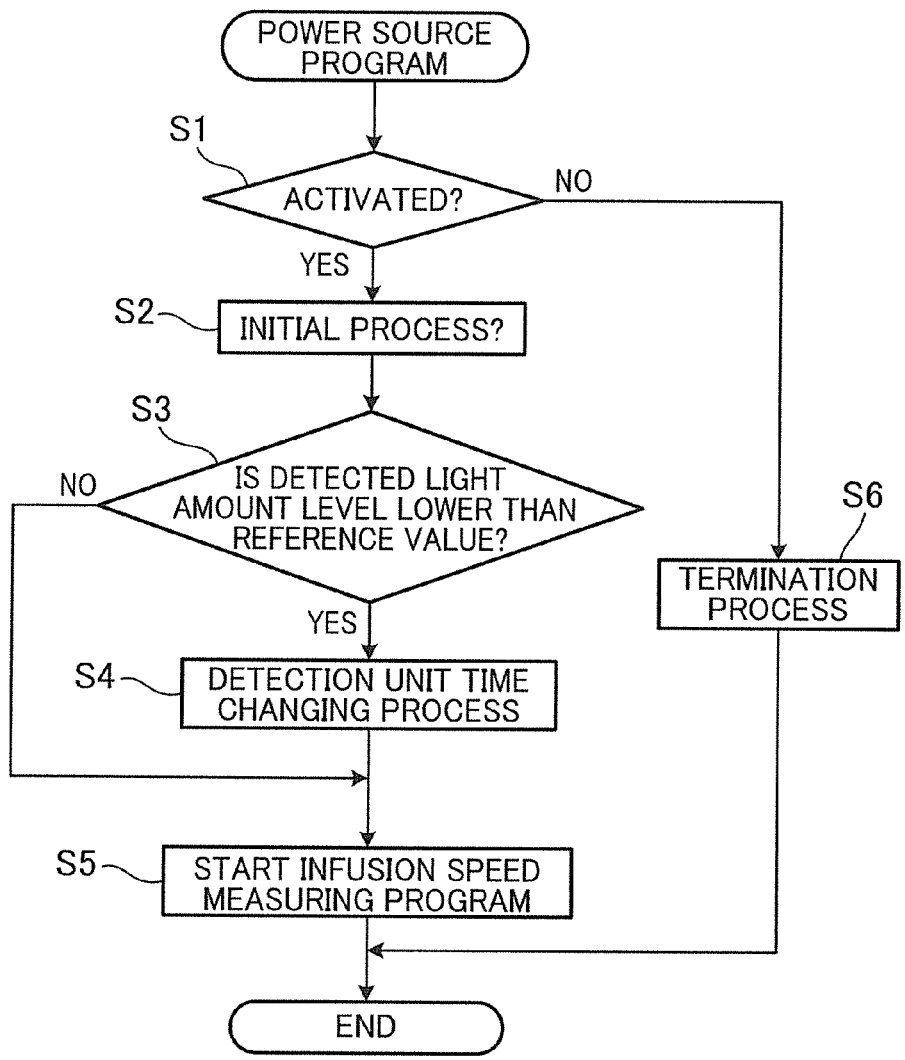
FIG. 9 is a flowchart of a power source program.

As shown in FIG. 9, to begin with, when the input unit 53 is operated, whether the infusion speed measurement instrument 1 is activated by this operation is determined (S1). When the infusion speed measurement instrument 1 is turned off by the operation (S1: NO), a process of terminating a later-described infusion speed measurement instrument program which is being independently run and devices such as the infusion fluid detector 13 and the information output unit 14 is carried out, and the power source is turned off (S6).

In the meanwhile, if the infusion speed measurement instrument 1 is turned on by the operation (S1: YES), the driving of the devices such as the infusion fluid detector 13 and the information output unit 14 starts (S2).

Then whether the light intensity level detected by the infusion fluid detector 13 is lower than a reference value is determined (S3). The state in which the light intensity level is lower than the reference value is a state in which the light emitting hole 10a or the light receiving hole 10b is covered with the users' hands or the like and hence the light receiver 13b cannot detect light. When the light intensity level of the light detected by the infusion fluid detector 13 is lower than the reference value (S3: YES), a detection unit time changing process is executed (S4). This detection unit time changing process is a process in which the unit time for the number of times of dropping is switched to 60 seconds or 10 seconds. To be more specific, an area for the unit time for the number of times of dropping is provided in the RAM 582, and information (unit time information) stored in the area is switched between information indicating 60 seconds and information indicating 10 seconds. The unit time information is read by the infusion speed measurement instrument program, and is used for calculating the infusion speed based on the number of times of dropping per the unit time.

In the meanwhile, when the light intensity level detected by the infusion fluid detector 13 is equal to or higher than the reference value (S3: NO) or after the step S4 is terminated, the infusion speed measurement instrument program starts (S5), and the power source program is terminated.

The driving of the information output unit 14 in the initial process (S2) may be executed after the step S4 (immediately before the step S5). With this, the user recognizes by the driving of the information output unit 14 that the change of the unit time has been completed.

Infusion Speed Measurement Program

The infusion speed measurement program which starts in the power source program will be described.

Figure 10:
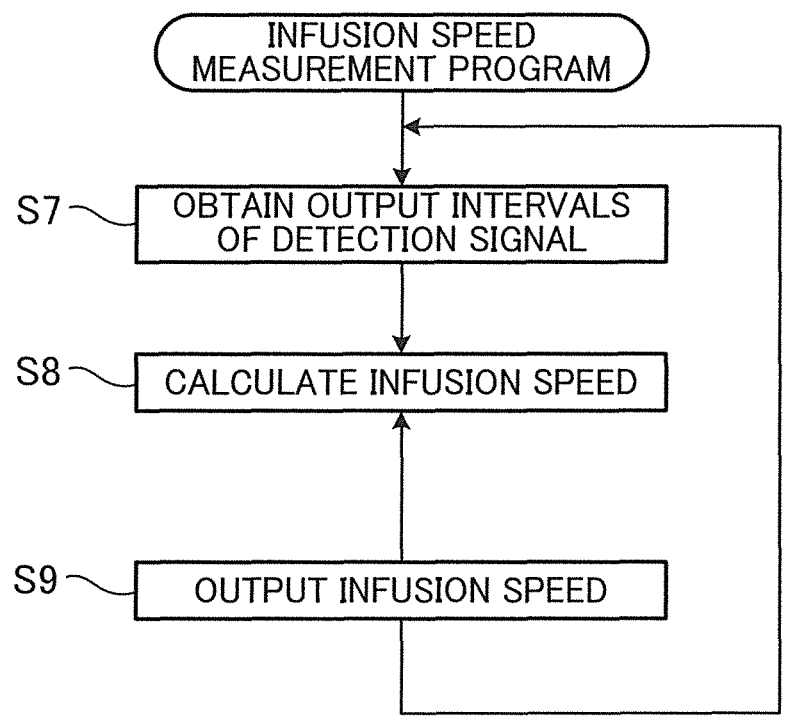
FIG. 10 is a flowchart of an infusion speed measurement program.

As shown in FIG. 10, when the infusion speed measurement program starts, output intervals of a detection signal are obtained (S7). The detection signal indicates a signal with a value lower than a predetermined detection reference value, among signals indicating light intensity levels sent from the light receiver 13b to the processing unit 59 via the filter section 60. That is to say, a signal, when the infrared light 24 heading from the light emitter 13a to the light receiver 13b is blocked by the infusion fluid 4 so that the light intensity level of the light received by the processing unit 59 is lower than the predetermined detection reference value, is obtained as the detection signal. Because the influence of disturbance light has been eliminated by the filter section 60 from the light intensity level received by the processing unit 59, the detection signal is determined based on the predetermined detection reference value, and the output intervals are easily specified. The detection reference value may be identical with or different from the reference value in the step S3. The output intervals may be calculated based on the time at which the detection signal is obtained, or may be calculated based on the time counted from the previous acquisition of the detection signal. Based on the output intervals, the infusion speed which is the number of times of dropping per the unit time is calculated (S8). In this regard, the unit time is determined based on the unit time information obtained from the RAM 582. The unit time information may be initially read to a register or the like, and obtained from the register thereafter. After the infusion speed is displayed by the information output unit 14 (S9), the program is executed again from S7.

Information indicating the acquisition of the detection signal, i.e., information indicating that the infusion fluid 4 has dropped may be output to the information output unit 14. For example, each time the detection signal is obtained, a dot, a mark, or the like may repeatedly be displayed on and disappear from the information output unit 14.

When the termination process (S6) is executed in the power source program, the infusion speed measurement program is interrupted and terminated. Furthermore, when, for example, the detection signal is not received (the infusion fluid is not detected) for a predetermined time, the termination process (S6) of the power source program may be executed to turn the power off.

Modifications

While the preferred embodiment of the present invention has been described, it should be noted that the scope of the invention is not limited to the above-described embodiment. For example, while the positioning contact part 11 is formed to be integrated with the housing 12, the positioning contact part 11 may include a height adjustment mechanism which is able to adjust the height of a part of the positioning contact part in contact with the flange part. To be more specific, for example, an arc-shaped groove (not illustrated) is formed outside (on the rear surface part 12b side of) the arc-shaped surface of the fitting recessed part 10 of the front surface part 12a of the housing 12 in the axial direction of the tunnel shape, plural arc-shaped plates (not illustrated) which can be attached to and detached from the groove are prepared, and the height adjustment is performed by replacing the arc-shaped plates.

In addition to the above, the fitting recessed part may be provided with a fixing elastic member, and the side wall of the drip chamber may be pinched by a force which is not lower than a predetermined holding force.

Figure 11:
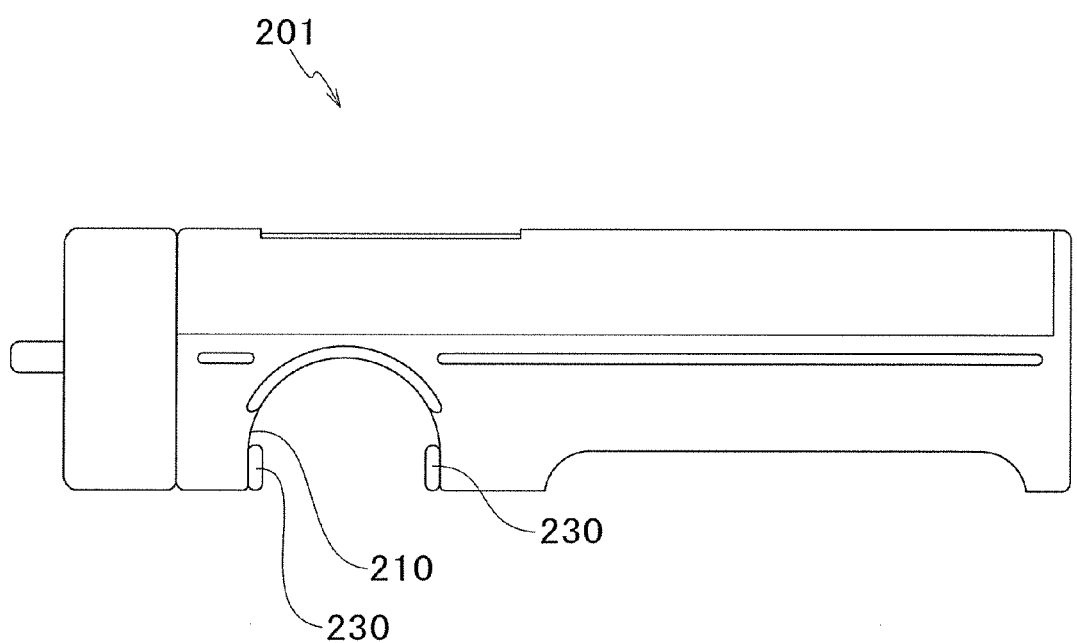
FIG. 11 shows a modification of the infusion speed measurement instrument.

To be more specific, in an infusion speed measurement instrument 201 shown in FIG. 11, two opposing fixing elastic members 230 are provided in a fitting recessed part 210. With this, when a drip chamber is fitted in the fitting recessed part 210, the side wall of the drip chamber is sandwiched by the holding force, which is not lower than the predetermined holding force, of the two fixing elastic members 230.

It is noted that only one side of the above opposing fixing elastic members may be provided with the fixing elastic members in the fitting recessed part 210, or the fixing elastic members may be provided along the arc.

As such, when the infusion speed measurement instrument 201 is attached to the drip chamber, the entirety or part of the weight of the infusion speed measurement instrument 201 is supported by the drip chamber thanks to the holding force exerted by the fixing elastic members 230·230. This reduces the burden on the user to maintain the infusion speed measurement instrument 201 to be attached to the drip chamber. In particular, when the fixing elastic members 230 hold the drip chamber with the holding force which is sufficient to support the entire weight of the infusion speed measurement instrument 201, the user is allowed to take his/her hand off from the infusion speed measurement instrument 201. The workability is excellent because the user is allowed to, for example, adjust the infusion speed through the clamp 73 by that hand.

The detailed description of the present invention provided hereinabove mainly focused on characteristics thereof for the purpose of easier understanding; however, the scope of the present invention shall be construed as broadly as possible, encompassing various forms of other possible embodiments, and therefore the present invention shall not be limited to the above embodiments.

Further, the terms and phraseology used in the present specification are adopted solely to provide specific illustration of the present invention, and in no case should the scope of the present invention be limited by such terms and phraseology. Further, it will be obvious to those skilled in the art that the other structures, systems, methods and the like are possible, within the spirit of the invention described in the present specification. The description of claims therefore shall encompass structures equivalent to the present invention, unless otherwise such structures are regarded as to depart from the spirit and scope of the present invention. To fully understand the object and effects of the present invention, it is strongly encouraged to sufficiently refer to disclosures of documents already made available.

REFERENCE SIGNS LIST

1 INFUSION SPEED MEASUREMENT INSTRUMENT
  2 DRIP CHAMBER
  4 INFUSION FLUID
  10 FITTING RECESSED PART
  11 POSITIONING CONTACT PART
  12 HOUSING
  13 INFUSION FLUID DETECTOR
  14 INFORMATION OUTPUT UNIT
  15 ANTI-ROLLING MEMBER
  19 WATERPROOF SEAL
  23 FLANGE PART
  23a LOWER SURFACE
  24 INFRARED LIGHT
  25 PASSING POINT
  31 PIPE
  32 PIPE
  32a DROPPING PORT
  121 PERIPHERAL WALL
  122 ONE-SIDE END FACE WALL
  123 OTHER-SIDE END FACE WALL

The invention claimed is:

1. An infusion speed measurement instrument configured to fit around a predetermined drip chamber having a side wall and a flange at an upper portion thereof and a drip pipe disposed therein, the infusion speed measurement instrument comprising:
  a housing having a cylindrical peripheral wall which includes a fitting recessed part formed therein so as to form a concave, drip-chamber-receiving tunnel that extends in a direction perpendicular to a longitudinal axis of the housing, the fitting recessed part being configured to receive therein the drip chamber with the sidewall of the drip chamber making contact with substantially the entire surface of the fitting recessed part, and with the configuration of the fitting recessed part, per se, being such as to hold the infusion speed measurement instrument on the drip chamber when the drip chamber is hung in an up-down direction;
  an infusion fluid detector, which is provided in the housing; which is configured to detect drops of infusion fluid dripping from a lower end of the drip pipe of the drip chamber; and which is fitted in the region of the fitting recessed part;
  an information output unit which is configured to output infusion information based on detection of the infusion fluid by the infusion fluid detector; and
  an upwardly protruding positioning contact part which is formed in the region of the fitting recessed part and which is configured such that when the infusion speed measurement instrument is installed on the drip chamber and positioned such that the positioning contact part makes contact with a lower surface of the flange of the drip chamber, the infusion fluid detector will be positioned along the sidewall of the drip chamber substantially at the level of the lower, drop-dripping end of the drip pipe.

2. The infusion speed measurement instrument according to claim 1, wherein the housing includes a one-side end face wall which closes a one-side end face of the peripheral wall, an other-side end face wall which closes an other-side end face of the peripheral wall, and an anti-rolling member which is formed by deforming a part of the peripheral wall in a radial direction.

3. The infusion speed measurement instrument according to claim 1, wherein the positioning contact part includes a height adjustment mechanism which is able to adjust the height of a part of the positioning contact part which makes contact with the flange when the infusion speed measurement instrument is installed on the drip chamber.

4. The infusion speed measurement instrument according to claim 1, wherein the configuration of the fitting recessed part, per se, which holds the infusion speed measurement instrument on the drip chamber includes a fixing elastic member which is provided in the fitting recessed part and which is configured to pinch the side wall of the drip chamber with force which is not lower than predetermined holding force.

5. An infusion speed measurement instrument configured to fit around a predetermined drip chamber having a side wall and a flange at an upper portion thereof and a drip pipe disposed therein, the infusion speed measurement instrument comprising:
  a housing which includes
    a cylindrical peripheral wall which includes a fitting recessed part formed therein so as to form a concave, drip-chamber-receiving tunnel that extends in a direction perpendicular to a longitudinal axis of the housing, the fitting recessed part being configured to receive therein the drip chamber with the sidewall of the drip chamber making contact with substantially the entire surface of the fitting recessed part, and with the configuration of the fitting recessed part, per se, being such as to hold the infusion speed measurement instrument on the drip chamber when the drip chamber is hung in an up-down direction,
    a one-side end face wall which closes a one-side end face of the peripheral wall, an other-side end face wall which closes an other-side end face of the peripheral wall, and
an anti-rolling member which is formed by deforming a part of the peripheral wall in a radial direction, and
a hanging member which is formed on the one-side end face wall, to which a string member is attachable;
an infusion fluid detector which is configured to detect, in a detection area arranged in the fitting recessed part, drops of infusion fluid dripping from an end of the drip pipe of the drip chamber when the drip chamber is fitted in the fitting recessed part;
an information output unit which is provided on the other-side end face wall side of the peripheral wall and which is configured to output infusion information based on detection of the infusion fluid by the infusion fluid detector; and
a switch member provided on the other-side end face wall of the housing, which is waterproof and configured to turn on or off power for driving the infusion fluid detector and the information output unit;
the housing further having an upwardly protruding positioning contact part which is formed in the region of the fitting recessed part and which is configured such that when the infusion speed measurement instrument is installed and positioned on the drip chamber so that the positioning contact part makes contact with a lower surface of the flange of the drip chamber, the infusion fluid detector will be positioned along the sidewall of the drip chamber substantially at the level of the lower, drop-dripping end of the drip pipe.

6. The infusion speed measurement instrument according to claim 5, wherein the positioning contact part includes a height adjustment mechanism which is able to adjust the height of a part of the positioning contact part which makes contact with the flange when the infusion speed measurement instrument is installed on the drip chamber.

7. The infusion speed measurement instrument according to claim 6, wherein the configuration of the fitting recessed part, per se, which holds the infusion speed measurement instrument on the drip chamber includes a fixing elastic member which is provided in the fitting recessed part and which is configured to pinch the side wall of the drip chamber with force which is not lower than predetermined holding force.

8. The infusion speed measurement instrument according to claim 2, wherein the positioning contact part includes a height adjustment mechanism which is able to adjust the height of a part of the positioning contact part which makes contact with the flange when the infusion speed measurement instrument is installed on the drip chamber.

9. The infusion speed measurement instrument according to claim 8, wherein the configuration of the fitting recessed part, per se, which holds the infusion speed measurement instrument on the drip chamber includes a fixing elastic member which is provided in the fitting recessed part and which is configured to pinch the side wall of the drip chamber with force which is not lower than predetermined holding force.

10. The infusion speed measurement instrument according to claim 1, wherein the positioning contact part comprises an arcuate portion protruding from the peripheral wall and extending along the fitting recessed part.

11. The infusion speed measurement instrument according to claim 5, wherein the positioning contact part comprises an arcuate portion protruding from the peripheral wall and extending along the fitting recessed part.

12. The infusion speed measurement instrument according to claim 1, wherein the positioning contact part includes an arc-shaped groove formed in the housing and an arc-shaped plate detachably provided in the arc-shaped groove.

13. The infusion speed measurement instrument according to claim 5, wherein the positioning contact part includes an arc-shaped groove formed in the housing and an arc-shaped plate detachably provided in the arc-shaped groove.

* * * * *